(12) United States Patent
Taniguchi et al.

(10) Patent No.: US 9,778,148 B2
(45) Date of Patent: Oct. 3, 2017

(54) ANALYSIS APPARATUS

(71) Applicant: HORIBA, Ltd., Kyoto-shi, Kyoto (JP)

(72) Inventors: Heihachiro Taniguchi, Kyoto (JP); Takuji Kurozumi, Kyoto (JP); Takahiro Yamada, Kyoto (JP); Yasushi Hirata, Kyoto (JP)

(73) Assignee: HORIBA, LTD., Kyoto-shi (JP)

( * ) Notice: Subject to any disclaimer, the term of this patent is extended or adjusted under 35 U.S.C. 154(b) by 0 days.

(21) Appl. No.: 14/975,970

(22) Filed: Dec. 21, 2015

(65) Prior Publication Data
US 2016/0187232 A1    Jun. 30, 2016

(30) Foreign Application Priority Data

Dec. 26, 2014  (JP) .................................. 2014-264184

(51) Int. Cl.
*G01N 1/22*      (2006.01)
*G01N 1/40*      (2006.01)
(Continued)

(52) U.S. Cl.
CPC ......... *G01N 1/2205* (2013.01); *G01N 1/4022* (2013.01); *G01N 31/12* (2013.01); *G01N 21/3504* (2013.01); *G01N 33/20* (2013.01)

(58) Field of Classification Search
CPC .... G01N 1/2205; G01N 1/4022; G01N 31/12; G01N 21/3504; G01N 33/20
(Continued)

(56) References Cited

U.S. PATENT DOCUMENTS 4,234,541 A * 11/1980 Bredeweg ............... G01N 31/12
                                                     134/166 C
4,772,454 A *  9/1988 Jarolics ................. G01N 1/2258
                                                     422/527
(Continued)

FOREIGN PATENT DOCUMENTS

CN       203615739 U    5/2014
JP       2000266740 A   9/2000
(Continued)

OTHER PUBLICATIONS

Extended European Search Report dated May 25, 2016; Application No./Patent No. 15201156.5-1554 Applicant: Horida, Ltd.: Total of 7 pages.

*Primary Examiner* — Hezron E Williams
*Assistant Examiner* — Marrit Eyassu
(74) *Attorney, Agent, or Firm* — Robert P. Michal, Esq.; Carter, DeLuca, Farrell & Schmidt, LLP

(57) ABSTRACT

In order to remove dust attached to a filter member 40 to surely clean the filter member 40, an analysis apparatus 100 includes: a sample containing part 10 that contains a sample; the filter member 40 through which gas produced from the sample heated in the sample containing part 10 passes; and a gas flow path L1 adapted to lead the gas having passed through the filter member 40 to an analyzer. In addition, the filter member 40 is formed in a tubular shape, and in one end part of the filter member 40, a gas lead-out port 40a connecting to the gas flow path L1 is formed. Further, it is configured that the gas passes through a side wall part 42 of the filter member 40 from outside to inside, and flows from the gas lead-out port 40a to the gas flow path L1.

5 Claims, 5 Drawing Sheets

(51) Int. Cl.
*G01N 31/12* (2006.01)
*G01N 21/3504* (2014.01)
*G01N 33/20* (2006.01)

(58) Field of Classification Search
USPC ........................................................ 73/28.04
See application file for complete search history.

(56) References Cited

U.S. PATENT DOCUMENTS

| | | | | |
|---|---|---|---|---|
| 5,039,322 | A * | 8/1991 | Holzl | B01D 46/2407 55/302 |
| 6,627,155 | B1 * | 9/2003 | Uemura | G01N 31/12 250/288 |
| 2005/0241416 | A1 * | 11/2005 | DeFriez | G01N 1/2258 73/863.12 |
| 2007/0180893 | A1 * | 8/2007 | Floor | G01N 1/2205 73/31.07 |
| 2009/0211370 | A1 * | 8/2009 | Ferri | G01N 1/2205 73/861.61 |
| 2012/0096925 | A1 * | 4/2012 | Hansen | G01N 1/2205 73/28.04 |
| 2013/0316465 | A1 * | 11/2013 | Steude | G01N 31/12 436/160 |

FOREIGN PATENT DOCUMENTS

| | | | |
|---|---|---|---|
| JP | 2000266741 A | * | 9/2000 |
| JP | 2000266741 A | | 9/2000 |
| JP | 2000338019 A | | 12/2000 |

* cited by examiner

ANALYSIS APPARATUS

CROSS REFERENCE TO RELATED APPLICATION

This Application claims the priority of Japanese Patent Application No. 2014-264184 filed on Dec. 26, 2014, which is incorporated by reference herein.

TECHNICAL FIELD

The present invention relates to an analysis apparatus such as an elemental analysis apparatus, which analyzes elements such as carbon (C) and sulfur (S) contained in a sample such as steel, nonferrous metal, or ceramic.

BACKGROUND ART

As this sort of analysis apparatus, for example, as disclosed in Patent Literature 1, there is known an analysis apparatus that heats a sample to thereby produce gas containing components in the sample, and analyzes the gas with an analyzer.

Specifically, the analysis apparatus is configured to include: a heating furnace that contains the sample inside; and a gas flow path that is formed above the heating furnace and adapted to lead the gas produced by heating the sample to the analyzer.

Meanwhile, the gas contains much dust, and therefore the above-described analysis apparatus is configured to provide a tubular-shaped filter above the heating furnace, and allow the gas to pass through a side wall part of the filter from inside to outside and flow to the gas flow path.

However, if the dust captured by the filter as described is left untouched, the dust does not only reduce the removal performance of the filter but allows the gas to adsorb to moisture and the like contained in the dust to reduce measurement accuracy and reduce a flow rate.

For this reason, in order to remove the dust captured by the filter, it may be possible to reversely jet cleaning gas from the above-described gas flow path. However, this method only removes dust attached to a part of the filter where the cleaning gas directly hits and to the periphery to the part, and it is difficult to remove the dust on the entire filter.

Further, as another configuration for removing dust, there is known a configuration where a brush is moved up and down along a filter. However, this configuration cannot solve the above-described problem because dust is pushed into the filter, and the dust in the filter may be difficult to remove.

CITATION LIST

Patent Literature

Patent Literature 1: JP-A2000-338019

SUMMARY OF INVENTION

Technical Problem

Therefore, the present invention is made in order to solve the above problem, and a main object thereof is to make it possible to easily remove dust on an entire filter.

Solution to Problem

That is, an analysis apparatus according to the present invention is an analysis apparatus including: a sample containing part that contains a sample; a filter member through which gas produced from the sample heated in the sample containing part passes; and a gas flow path adapted to lead the gas having passed through the filter member to an analyzer. In addition, the filter member is formed in a tubular shape, and in one end part of the filter member, a gas lead-out port connecting to the gas flow path is formed. Further, it is configured that the gas passes through a side wall part of the filter member from outside to inside, and flows from the gas lead-out port to the gas flow path.

In such an analysis apparatus, since the filter member is formed in the tubular shape, the inner circumferential surface of the side wall part of the filter member is larger than the outer circumferential surface, and therefore by making the gas pass through the side wall part from outside to inside, more dust can be captured.

In this case, in order to remove the dust captured by the filter member, for example, cleaning gas is made to pass from inside the filter member to outside. At this time, when supplying the cleaning gas to the inside the filter member through, for example, the gas lead-out port, the cleaning gas reaches throughout the filter member, and pressure inside the filter member increases. As a result, the cleaning gas powerfully flows from inside to outside throughout the side wall part of the filter member, and thereby the dust on the entire filter member can be easily removed.

As described, the above-described analysis apparatus can easily remove the dust on the entire filter member without the use of a cleaning brush by making the cleaning gas pass from inside the filter member to outside. Although in the past, a driving mechanism for a cylinder or the like has been provided above a sample containing part in order to move a brush up and down, the above-described configuration makes it possible to effectively utilize space around the sample containing part instead of using the driving mechanism.

As a specific embodiment for surely cleaning the dust attached to the filter member, preferably, the analysis apparatus further includes a cleaning gas supply mechanism that supplies cleaning gas for cleaning the filter member to the inside the filter member from a cleaning gas supply port formed in the one end part of the filter member, and it is configured that the cleaning gas supplied by the cleaning gas supply mechanism passes through the side wall part of the filter member from inside to outside.

As described above, the gas passes through the side wall part of the filter member from outside to inside, and therefore the gas containing dust flows in from outside the filter member.

For this reason, preferably, the filter member is provided above the sample; and the sample containing part has a tubular member that contains inside the filter member from a lower end part to an upper end part of the filter member together with the sample and is formed of a single member.

In such a configuration, since the tubular member formed of a single member contains the filter member from the lower end part to the upper end part of the filter member together with the sample, in the case where some of the dust contained in the gas before passing through the filter member is attached to the inner surface of the tubular member, for example, by replacing the tubular member or removing the tubular member to clean it, the dust attached to the periphery of the filter member can be easily removed.

Preferably, the sample containing part has: a heating furnace main body that heats the sample; a lid body that is detachably attached to the upper part of the heating furnace main body and holds the filter member as well as rotating around an axis along a direction of the attachment/detachment; and a removal assisting mechanism that is provided between the heating furnace main body and the lid body, and converts force applied to the lid body in a rotational direction to force in a vertical direction to assist removal of the lid body.

In the case of, when removing the lid body from the heating furnace main body, for example, applying large power in a direction of the removal, the lid body may be tilted by impact produced at the time of the removal. As a result, the filter member held by the lid body may contact with the inner surface of the heating furnace main body to damage the inner surface of the heating furnace main body and/or the filter member.

On the other hand, in the above-described configuration, since the removal assisting mechanism adapted to assist the removal of the lid body is provided between the heating furnace main body and the lid body, the lid body can be easily removed by rotating the lid body with respect to the heating furnace main body. As a result, the lid body can be removed from the heating furnace main body without being tilted, and therefore the above-described problem is unlikely to occur.

Also, an analysis apparatus according to the present invention includes: a sample containing part that contains a sample; a filter element through which gas produced from the sample heated in the sample containing part passes; an analyzer that analyzes the gas having passed through the filter element; and a cleaning gas supply path adapted to supply cleaning gas for cleaning the filter element to an inside the filter element from one end opening of the filter element.

In such an analysis apparatus, since the cleaning gas is supplied to the inside the filter element from the one end opening of the filter element, the cleaning gas can be flowed along an axial direction of the filter element. In doing so, the cleaning gas does not hit part of the filter element but reaches throughout the filter element to increase pressure inside the filter element. As a result, the cleaning gas powerfully flows throughout the filter element from inside toward outside, and thereby dust on the entire filter element can be easily removed.

Advantageous Effects of Invention

According to the present invention configured as described, the cleaning gas is supplied to the inside the filter member, and thereby dust attached to the filter member can be removed to surely clean the filter member.

DESCRIPTION OF EMBODIMENTS

In the following, one embodiment of an analysis apparatus according to the present invention will be described with reference to drawings.

Figure 1:
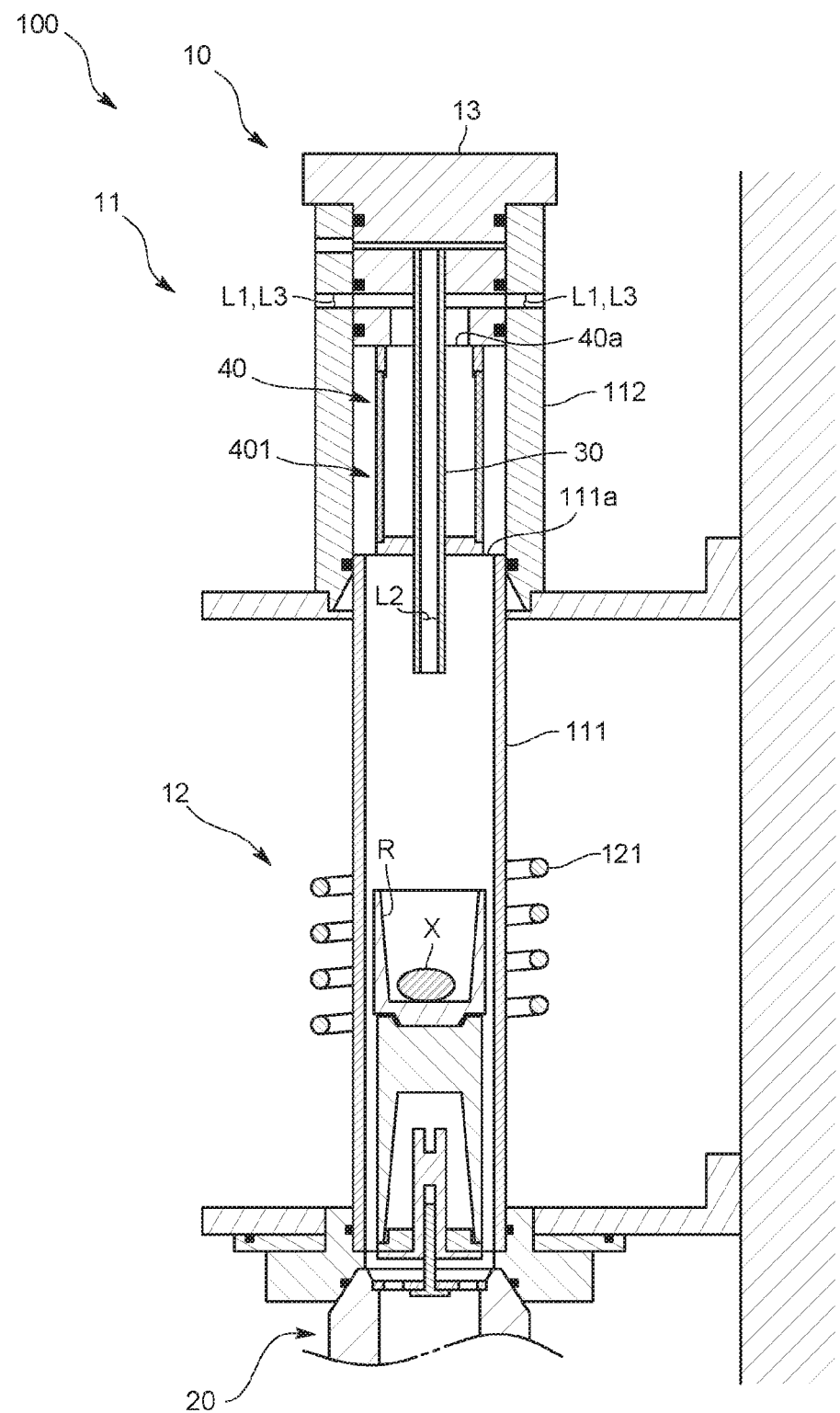
FIG. 1 is a diagram schematically illustrating the overall configuration of an analysis apparatus in the present embodiment.

An analysis apparatus 100 according to the present embodiment is an elemental analysis apparatus that analyzes elements such as carbon (C) and sulfur (S) contained in a sample X such as steel, nonferrous metal, or ceramic, and as illustrated in FIG. 1, includes: a heating furnace 10 as a sample containing part adapted to contain the sample X; and an unillustrated analyzer adapted to measure gas (hereinafter also referred to as measurement gas) produced by heating the sample X.

First, the unillustrated analyzer will be described.

The analyzer is one that analyzes the measurement gas led to the analyzer to obtain the contents of respective components contained in the sample X, and makes the analysis using a non-dispersive infrared absorption method (NDIR method). Specifically, the analyzer has an unillustrated non-dispersive infrared detector, and detects $CO_2$, CO, $SO_2$, and the like contained in the measurement gas to thereby obtain the contents of carbon (C), sulfur (S), and the like contained in the sample X.

Next, the heating furnace 10 will be described.

The heating furnace 10 is one that contains the sample X inside to heat the sample X, and thereby produces the measurement gas containing the components in the sample X, and as illustrated in FIG. 1, has a heating furnace main body 11 and a heating mechanism 12 provided around the heating furnace main body 11.

The heating furnace main body 11 has: a tubular member 111 that is formed of a single member such as quartz glass and formed in, for example, a straight tubular shape having a cross-sectionally circular shape; and a block body 112 provided above the tubular member 111, and inside the heating furnace main body 11, a crucible R containing the sample X is placed.

The crucible R is made of a magnetic material such as ceramic, and vertically moved by a vertical movement mechanism 20 provided below the crucible R between a heating position where the sample X is heated in the heating furnace 10 and a retreat position where the sample X retreats outside the heating furnace 10.

The block body 112 is one having opened upper and lower ends, inside which an internal space communicatively connecting these openings is formed. Here, the block body 112 is formed in a substantially rotating body shape, and the lower end opening is airtightly fitted with the upper end part of the tubular member 111 through a sealing member or the like.

In the present embodiment, the internal space of the block body 112 and the internal space of the tubular member 111 coincide in terms of central axis with each other, and these internal spaces are connected to each other through the upper end opening 111a of the tubular member 111.

Also, the upper end opening of the block body 112 is detachably attached with a lid body 13 through a sealing member or the like.

The heating mechanism 12 is one that generates induction current in the sample X contained in the crucible R and heat the sample X by using a high-frequency induction heating method, and as illustrated in FIG. 1, includes a coil 121, and an unillustrated power supply adapted to apply high frequency AC voltage to the coil 121. In this embodiment, the coil 121 is provided along the outer circumference of the heating furnace main body 11, and it is configured that when the high frequency AC voltage is applied to the coil 121, the crucible R is positioned inside the coil 121 by the above-described vertical movement mechanism 20. In addition, when the high frequency AC voltage is applied to the coil 121, a heat accelerator such as tungsten loaded into the crucible R is heated to accelerate the heating of the sample X.

The analysis apparatus 100 in the present embodiment further has: a gas flow path L1 adapted to lead the measured gas produced in the heating furnace 10 to the unillustrated analyzer; and an oxygen supply path L2 adapted to supply oxygen into the heating furnace 10.

Figure 2:
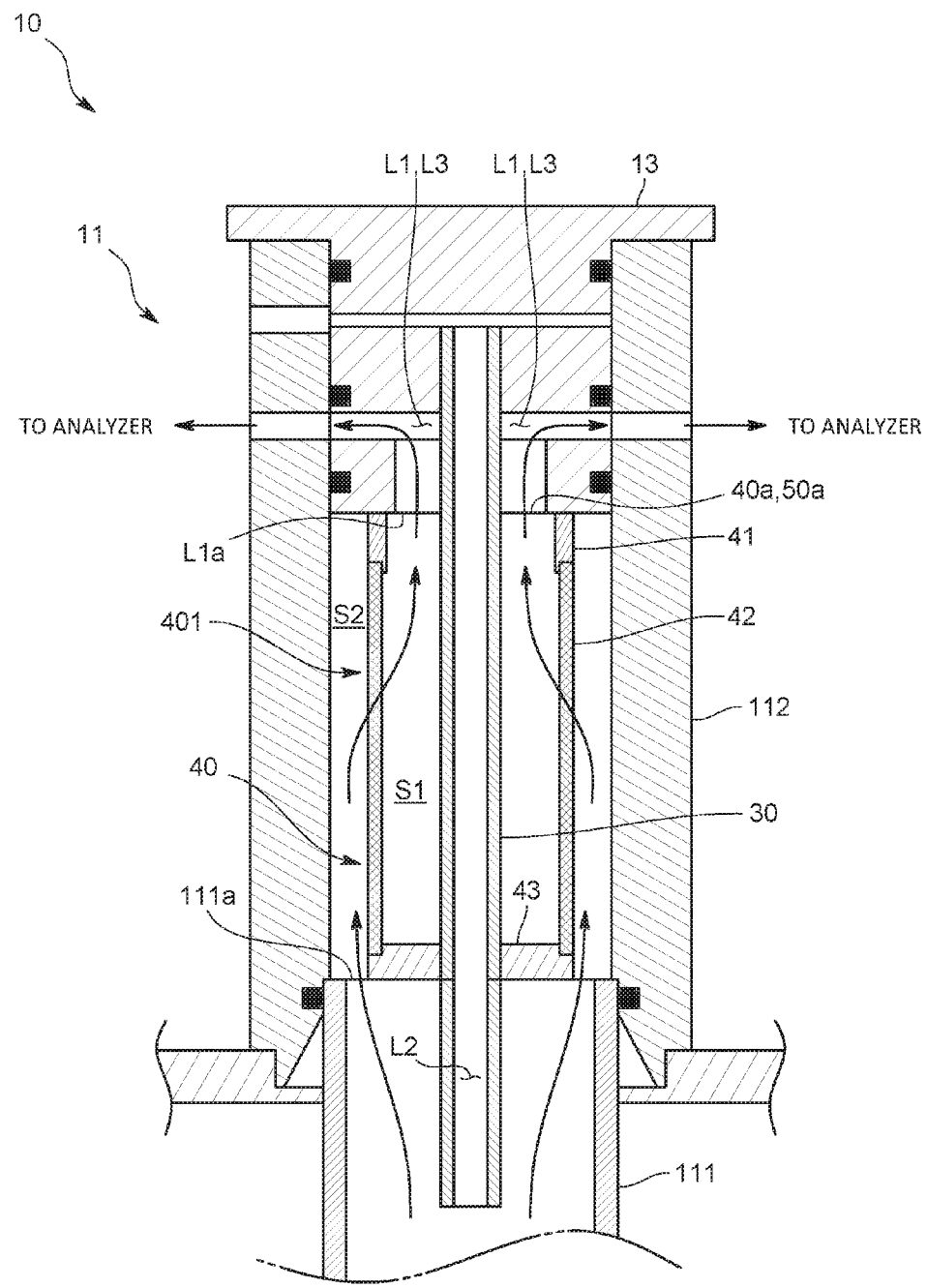
FIG. 2 is a diagram schematically illustrating a filter member in the same embodiment.

As illustrated in FIGS. 1 and 2, the gas flow path L1 is one that connects the internal space of the heating furnace 10 and the unillustrated analyzer to each other, and one end opening L1a thereof is communicatively connected to the internal space of the heating furnace 10. The one end opening L1a is provided in a surface forming the internal space of the heating furnace 10, and in the present embodiment, formed in the upper wall part of the heating furnace 10.

More specifically, part of the above-described gas flow path L1 is provided in the block body 112 and the lid body 13 constituting the heating furnace 10, and the one end opening L1a is formed in the bottom surface of the lid body 13, and formed in, for example, a circular shape.

The oxygen supply path L2 is one adapted to supply oxygen from an unillustrated oxygen cylinder into the heating furnace 10, and specifically, formed of a supply path forming member 30 formed in, for example, a straight tubular shape having a cross-sectionally circular shape.

As illustrated in FIGS. 1 and 2, the supply path forming member 30 is held by the upper wall part (in the present embodiment, the lid body 13) of the heating furnace 10 such that the central axis of an internal space thereof coincides with the central axis of the internal space of the tubular member 111, and the lower end part thereof is positioned above the crucible R. This makes it possible to supply oxygen flowing through the oxygen supply path L2 mainly into the crucible R. In addition, the supply path forming member 30 in the present invention is arranged such that the central axis of the internal space thereof passes through the center of the above-described one end opening L1a.

Note that the supply path forming member 30 in the present embodiment is also used to, for example, supply purge gas such as oxygen into the heating furnace 10 when purging the inside the heating furnace 10.

In addition, as illustrated in FIG. 2, the analysis apparatus 100 in the present invention further includes a tubular-shaped filter member 40 provided in the heating furnace 10, and is configured such that the measurement gas passes through the side wall part 401 of the filter member 40 from outside to inside.

The filter member 40 is provided so as to surround the above-described one end opening L1a of the gas flow path L1, and configured to lead out the measured gas having passed through the side wall part 401 to the gas flow path L1 through a gas lead-out port 40a formed in an upper end part.

The filter member 40 in the present embodiment is provided in the block body 112 to partition the internal space of the block body 112 into an inner internal space S1 and an outer internal space S2, and the inner internal space S1 is communicatively connected with the gas flow path L1, whereas the outer internal space S2 is communicatively connected with the internal space of the tubular member 111. That is, in the present embodiment, the one end opening L1a of the gas flow path L1 opens to the inner internal space S1, whereas the upper end opening 111a of the tubular member 111 opens to the outer internal space S2, and the measurement gas having flowed from the upper end opening 111a into the outer internal space S2 passes through the side wall part 401 to flow to the inner internal space S1, and is led to the gas flow path L1 through the gas lead-out port 40a.

Specifically, the filter member 40 includes: a tubular filter element 42 forming at least part of the side wall part 401; and upper and lower holding members 41 and 43 that hold the filter member 42 from above and below, respectively.

The filter element 42 is one that is prepared by, for example, forming multiple metallic wire members in a net shape, and in this embodiment, formed in a cylindrical shape of which both ends open. The outside diameter of the filter element 42 is smaller than the inside diameter of the tubular member 111, and when viewed from above, inside the block body 112, the tubular member 111 is provided, inside which the filter element 42 is provided.

The upper holding member 41 is one that holds the filter element 42 with the lower holding member 43 with the upper end part thereof attached to the upper wall part (in the present embodiment, the lid body 13) of the heating furnace 10, and in the upper end part, the above-described gas lead-out port 40a is formed.

The gas lead-out port 40a is formed in a circular shape, and in this embodiment, the upper holding member 41 is attached to the lid body 13 such that the gas lead-out port 40a and the one end opening L1a of the gas flow path L1 concentrically overlap each other.

Note that the gas lead-out port 40a is larger in diameter than the one end opening L1a, and inside the gas lead-out port 40a, the one end opening L1a is positioned.

The lower holding member 43 is one for protecting the filter element 42 from dust such as soot produced by heating the sample X and the heat accelerator, and blocks the lower end opening of the filter element 42 as well as compressing the filter element 42 to fix it with the upper holding member 41 without the use of a sealing member or the like.

The lower holding member 43 in the present embodiment is made of metal having a heat transfer property, and configured to transfer heat transferring from below to the filter element 42.

In the lower holding member 43, a through-hole through which the above-described supply path forming member 30 penetrates is formed, and in a state where the supply path forming member 30 penetrates through the through-hole, the filter member 40 and the supply path forming member 30 are provided with the central axes thereof coinciding with each other.

In doing so, the heating furnace main body 11, block body 112, filter member 40, and supply path forming member 30 are arranged such that the central axes of the internal spaces of them coincide with each other, and when viewed from above, these internal spaces concentrically overlap one another.

In the above-described configuration, as illustrated in FIG. 2, the measurement gas moves up from the crucible R to reach the upper end opening 111a of the tubular member 111, and passes through the gap between the tubular member 111 and the lower holding member 43 to flow into the outer internal space S2 formed between the filter member 40 and the block body 112. Then, the measurement gas passes through the filter element 42 from outside to inside, and flows to the inside the filter member 40, i.e., flows into the inner internal space S1. In doing so, the dust contained in the measurement gas is captured by the outer circumferential surface of the filter element 42. The measurement gas having passed through the filter element 42 flows into the gas flow path L1 through the gas lead-out port 40a, and is led into the unillustrated analyzer.

In addition, the analysis apparatus 100 in the present embodiment further includes a cleaning gas supply mechanism adapted to supply cleaning gas for cleaning the dust captured by the filter member 40 to the inside the filter member 40 from a cleaning gas supply port 50a formed above the filter member 40.

Specifically, the cleaning gas supply mechanism includes: an unillustrated cleaning gas cylinder; and a cleaning gas supply path L3 adapted to lead the cleaning gas to the cleaning gas supply port 50a.

The cleaning gas supply path L3 is one adapted to supply the cleaning gas from the upper end opening of the filter element 42 to the inside the filter element 42, and in the present embodiment, configured to supply the cleaning gas to the inside the filter element 42 along the axial direction of the filter element 42.

In the present embodiment, the cleaning gas supply port 50a and the gas lead-out port 40a are integrated, and the cleaning gas supply path L3 and the gas flow path L1 are integrated.

That is, the cleaning gas supply mechanism in the present embodiment is configured to flow the cleaning gas in a direction opposite to the flow direction of the measurement gas. In doing so, the cleaning gas supplied from the cleaning gas cylinder flows through the gas flow path L1, then is led to the gas lead-out port 40a, and is jetted into the filter member 40 through the gas lead-out port 40a.

The intermediate work between the end of the analysis of the sample X and the start of analysis of a next sample X will now be briefly described.

When the analysis of the sample X ends, as described above, the cleaning gas such as nitrogen is supplied to the inside the filter member 40 through the cleaning gas supply path L3 to remove the dust captured by the filter element 42. Note that the present embodiment is adapted to supply the cleaning gas every time after analysis; however, it is not necessarily required to supply the cleaning gas every time.

Subsequently, the heating furnace 10 is opened, and also the crucible R in the heating position is moved to the retreat position by the vertical movement mechanism 20. At this time, if removed dust or the like is on the bottom or the like of the heating furnace 10, the dust or the like is removed.

Then, the crucible R is replaced with a crucible R containing the sample X to be analyzed next, then the new crucible R is moved to the heating position by the vertical movement mechanism 20, and the heating furnace 10 is closed.

Finally, the purge gas such as oxygen is flowed into the heating furnace 10 and the intermediate work is ended.

The analysis apparatus 100 according to the present embodiment configured as described is configured such that the measurement gas passes through the filter element 42 from outside to inside, and therefore the cleaning gas can be jetted into the filter member 40 so as to flow in the opposite direction to the flow of the measurement gas. In doing so, the cleaning gas supplied into the filter member 40 reaches throughout the inside the filter member 40. As a result, pressure inside the filter member 40 increases, and thereby the cleaning gas starts to powerfully flow through the filter element 42 from inside toward outside, making it possible to easily remove the dust captured by the filter element 42.

More specifically, since the cleaning gas is supplied from above the filter member 40 through the cleaning gas supply port 50a, the cleaning gas hits the lower holding member 43 facing to the cleaning gas supply port 50a, and thereby diffuses. In doing so, the cleaning gas can reach throughout the inside the filter member 40 to completely remove the dust captured by the filter element 42.

Also, the above-described configuration makes it possible to eliminate the need for a brush for removing dust and a driving mechanism for vertically moving the brush as have been conventionally used.

This makes it possible to effectively utilize the space around the heating furnace 10, where the driving mechanism has been conventionally installed.

Also, since the filter element 42 is formed in the circular shape, the outer circumferential surface is larger than the inner circumferential surface, and as compared with the case where the measurement gas passes through the filter element 42 from inside to outside, the case where the measurement gas passes through the filter element 42 from outside to inside makes it possible to capture much dust.

Further, since the lower holding member 43 for the filter member 40 has the heat transfer property, heat transferring from the crucible R and the sample X can be transferred to the filter element 42 through the lower holding member 43. This makes it possible to evaporate moisture, water droplets, and the like attached to the filter element 42 to prevent the measurement gas from being adsorbed by the moisture, water droplets, and the like, and thereby a measurement error can be reduced.

Also, since the cleaning gas supply path L3 and the gas flow path L1 are integrated, and the cleaning gas supply port 50a and the gas lead-out port 40a are integrated, the block body 112 and the filter member 40 can be easily manufactured.

In addition, since the supply path forming member 30 and the filter member 40 are attached to the lid body 13, the supply path forming member 30 and the filter member 40 can be attached/detached together with the lid body 13, and therefore as compared with a configuration where the respective members must be individually attached/detached, maintainability can be improved.

Still in addition, since the block body 112 and the filter member 40 are arranged such that the central axes of the internal spaces of them coincide with each other, the measurement gas passes through the filter element 42 of the filter member 40 from outside toward inside along the circumferential direction without unevenness. As a result, the filter element 42 can efficiently capture the dust in the measurement gas.

Further in addition, since the filter member 40 and the supply path forming member 30 are arranged such that the central axes of the internal spaces of them coincide with each other, the cleaning gas passes through the filter element 42 of the filter member 40 from inside toward outside along the circumferential direction without unevenness. As a result, the cleaning gas can remove the dust captured by the filter element 42 along the circumferential direction without unevenness.

Note that the present invention is not limited to the above-described embodiment.

In the above-described embodiment, it is configured that the upper end part of the tubular member 111 is airtightly fitted into the lower end part of the block body 112. In such a configuration, the inner surfaces of the tubular member 111 and the block body 112 are attached with dust because the gas containing the dust flows outside the filter member 40.

Figure 3:
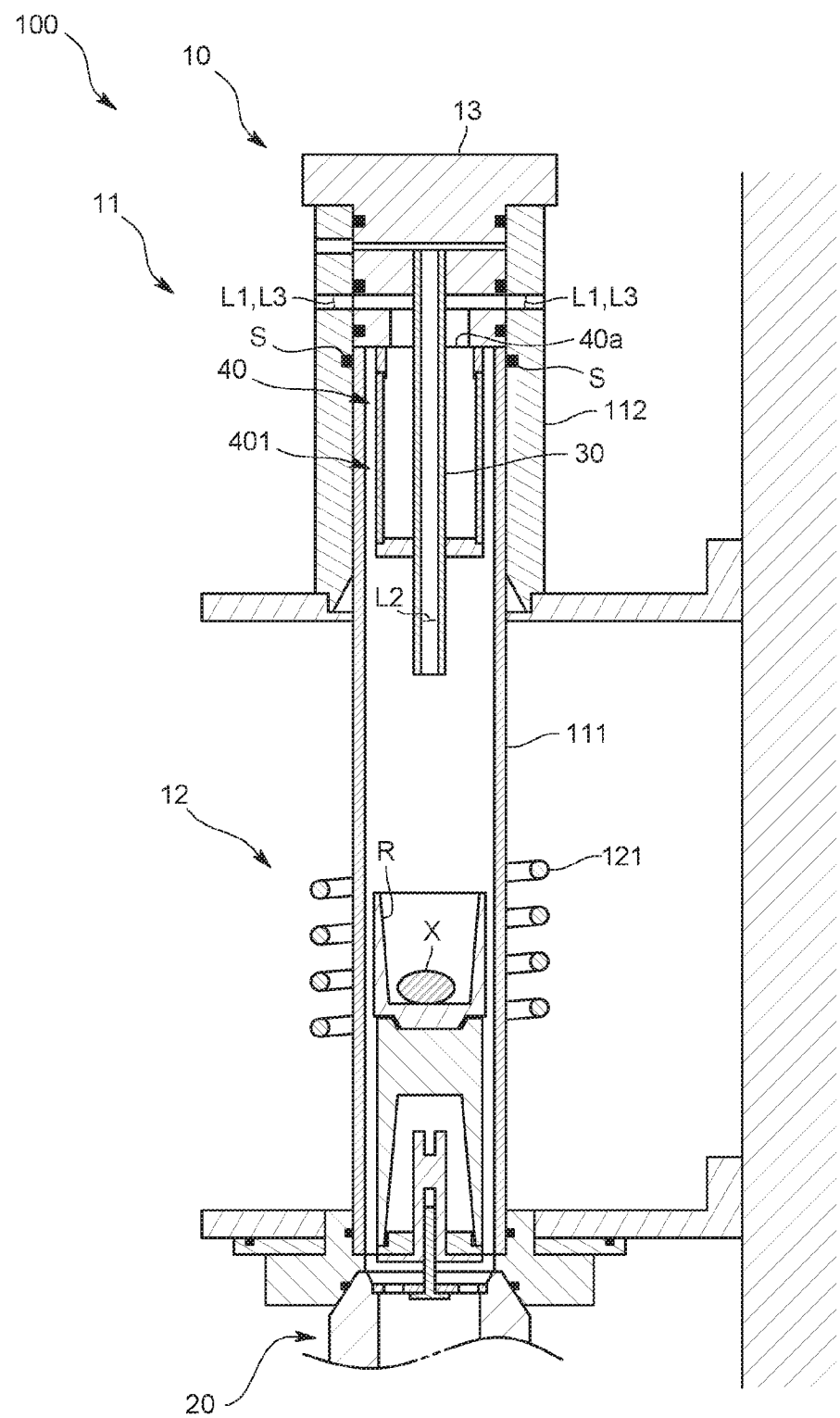
FIG. 3 is a diagram schematically illustrating the overall configuration of an analysis apparatus in a variation.

For this reason, as illustrated in FIG. 3, preferably, it is configured that the upper end part of the tubular member 111 formed of a single member extends to the lid body 13 positioned above the block body 12. In this configuration, the heating furnace main body 11 contains the filter member 40 from its lower end part to its upper end part.

In the above-described configuration, although dust contained in the measurement gas is attached to the inner surface of the tubular member 111, since the tubular member 111 is formed of a single member, for example, replacing the tubular member 111 or removing and cleaning the tubular member 111 makes it possible to easily remove dust attached around the filter member 40.

Also, when dust is attached to the inner wall of the block body 112, the dust may not be easily removed depending on the material or shape of the block body 112. However, the above-described configuration makes it possible to prevent the easy attachment of dust to the inner wall of the block body 112 to prevent the block body 112 from getting dirty because the upper end part of the tubular member 111 extends to the lid body 13.

Further, since the upper end part of the tubular member 111 extends to the lid body 13, in a state where the lid body 13 is removed from the block body 112, the distance from the upper end opening of the block body 112 to the upper end of the tubular member 111 is short, and therefore the tubular member 111 can be easily removed.

In addition, since the upper end part of the tubular member 111 extends to the lid body 13, as illustrated in FIG. 3, the sealing member S provided between the tubular member 111 and the block body 112 can be provided near the lid body 13. For this reason, the sealing member S can be kept away from the heating mechanism 12 to reduce the effect of heat from the heating mechanism 12, and therefore the life of the sealing member S can be elongated.

On the other hand, in the above-described configuration, for example, if the lid body 13 tilts when removing the lid body 13, the filter member 40 hung from the lid body 13 may contact with a glass tube as the tubular member 111, and this may damage a contact point.

Figure 4:
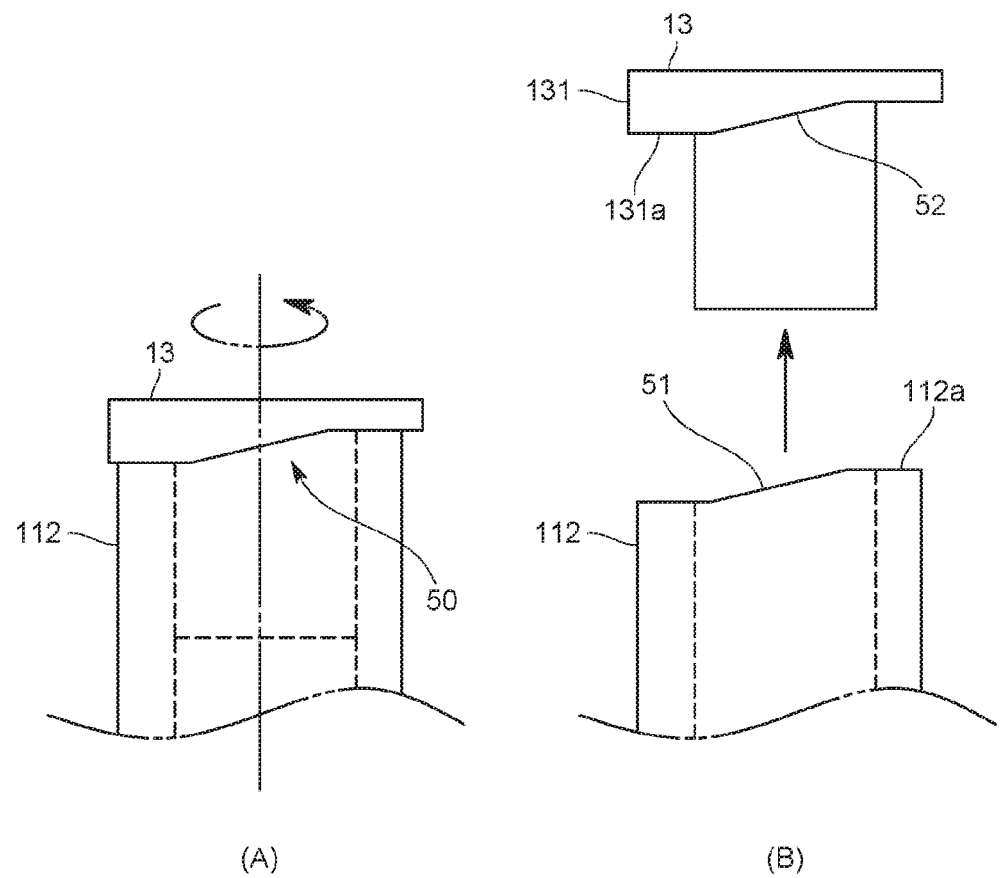
FIG. 4 is a diagram schematically illustrating a removal assisting mechanism in another variation.

For this reason, as illustrated in FIG. 4, preferably, the lid body 13 is configured to rotate with respect to the block body 112 to be thereby attached/detached to/from the upper end opening of the block body 112, and between the lid body 13 and the block body 112, a removal assisting mechanism 50 adapted to assist the removal of the lid body 13 is provided.

As illustrated in FIGS. 4A and 4B, the removal assisting mechanism 50 is one that converts force applied to the lid body 13 in a rotational direction to force in a vertical direction (removing direction) to assist the removal of the lid body 13.

Specifically, as illustrated in FIG. 4B, the removal assisting mechanism 50 is configured to include: a guiding surface 51 that is provided on the block body 112 and tilted with respect to the axial direction; and a guided surface 52 that is provided on the lid body 13 and slidingly moves on the guiding surface 51 when rotating the lid body 13 with respect to the block body 112.

In the present embodiment, the guiding surface 51 is formed as part of the upper surface 112a of the block body 112, and the guided surface 52 is formed as part of the lower surface 131a of a flange part 131 of the lid body 13.

In the above-described configuration, when rotating the lid body 13 with respect to the block body 112, the guided surface 52 slidingly moves on the guiding surface 51 while contacting with the guiding surface 51. In doing so, the force applied to the lid body 13 in the rotational direction is converted to the force in the vertical direction (removal direction), and thereby the lid body 13 can be easily removed.

Such a configuration makes it possible to remove the block body 112 without tilting the lid body 13, and therefore the tubular member 111 and the like are not at risk of being damaged.

Figure 5:
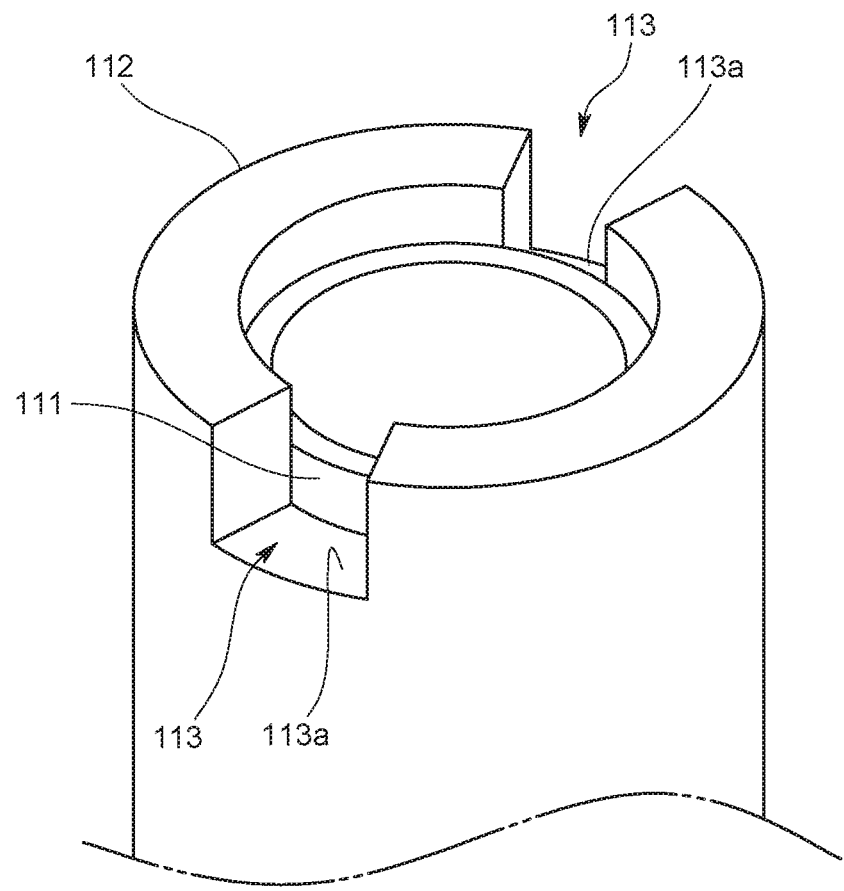
FIG. 5 is a diagram schematically illustrating a block body in still another variation.

Also, in order to more easily remove the tubular member 111 in the configuration where the upper end part of the tubular member 111 extends to the lid body 13 or to the vicinity of the lid body 13 as described above, as illustrated in FIG. 5, the block body 112 is preferably formed such that on the upper end surface thereof, multiple step parts 113 are formed.

More specifically, the step parts 113 are formed by cutting out the upper part of the block body 112 in a thickness direction, and configured such that the bottom surfaces 113a of the respective step parts 113 are positioned below the upper end of the tubular member 111.

In doing so, in a state where the lid body 13 is removed from the block body 112, the tubular member 111 can be picked with, for example, fingers inserted from the step parts 113, and thereby the tubular member 111 can be more easily removed to improve maintainability.

Further, the filter member in the above-described embodiment is formed in the tubular shape having the cross-sectionally circular shape, but may be formed in a tubular shape having a cross-sectionally rectangular or polygonal shape.

In addition, the filter element in the above-described embodiment is provided around the entire circumference of the side wall part of the filter member, but may be provided on parts of the side wall part such as being intermittently provided on the side wall part along the circumference direction of the filter member.

Still in addition, the filter member, the supply path forming member, and the lid body may be integrally formed.

This makes it possible to simultaneously remove the filter member and the supply path forming member by removing the lid body from the block body, and thereby maintainability can be improved.

Note that the term "integrally" herein is not necessarily required to be formed of a single member but also includes the case where the respective members are mechanically connected.

The cleaning gas supply port in the above-described embodiment is formed integrated with the gas lead-out port, but may be formed separately from the gas lead-out port, or part of the cleaning gas supply port may be formed integrated with the gas lead-out port.

The cleaning gas supply path in the above-described embodiment is formed integrated with the gas flow path, but may be formed separately from the gas flow path, or part of the cleaning gas supply path may be formed integrated with the gas flow path.

As a specific embodiment, an embodiment such as one where part of the cleaning gas supply path is formed in the upper holding member can be cited.

Also, in the filter member in the above-described embodiment, part of the side wall part is formed of the filter element. However, not only the side wall part, but the whole or part of the lower holding member may be formed of a filter element.

Besides, obviously, the present invention is not limited to any of the above-described embodiment and variations, but can be variously modified without departing from the scope thereof.

REFERENCE SIGNS LIST

100: Analysis apparatus
10: Heating furnace

11: Heating furnace main body
13: Lid body
40: Filter member
50a: Cleaning gas supply port
L1: Gas flow path
L3: Cleaning gas supply path
X: Sample

The invention claimed is:

1. An analysis apparatus comprising:
a heating furnace comprising a heating furnace main body having a tubular member and a block body provided above the tubular member, the heating furnace containing a sample;
a filter member through which gas produced from the sample heated in the heating furnace passes; and
a gas flow path which leads the gas having passed through the filter member to an analyzer,
wherein the filter member is formed in a tubular shape, and the filter member comprises in one end part a gas lead-out port connecting to the gas flow path, and the filter member is provided in the block body to partition an internal space of the block body into an inner internal space and an outer internal space, wherein the inner internal space is communicatively connected with an internal space of the tubular member, such that the gas passes through a side wall part of the filter member from the outer internal space to the inner internal space and flows from the gas lead-out port to the gas flow path, and
wherein the filter member comprises:
a filter element formed in a tubular shape; and
a lower holding member which holds the filter element, wherein the lower holding member holds a supply path forming member which is arranged inside the inner internal space.

2. The analysis apparatus according to claim 1, further comprising a cleaning gas supply mechanism that supplies cleaning gas for cleaning the filter member to an inside the filter member from a cleaning gas supply port formed in the one end part of the filter member,
wherein it is configured that the cleaning gas supplied by the cleaning gas supply mechanism passes through the side wall part of the filter member from inside to outside.

3. The analysis apparatus according to claim 1, wherein:
the filter member is provided above the sample; and
the sample containing part has a tubular member that contains the filter member, from an lower end part to an upper end part of the filter member, as well as the sample, and is formed of a single member.

4. The analysis apparatus according to claim 1, wherein the sample containing part has:
a heating furnace main body that heats the sample;
a lid body that is detachably attached to an upper part of the heating furnace main body, and holds the filter member as well as rotating around an axis along a direction of the attachment/detachment; and
a removal assisting mechanism that is provided between the heating furnace main body and the lid body, and converts force applied to the lid body in a rotational direction to force in a vertical direction and assists removal of the lid body.

5. An analysis apparatus comprising:
a sample containing part that contains a sample;
a filter element through which gas produced from the sample heated in the sample containing part passes, the filter element being formed in a tubular shape;
a lower holding member which holds the filter element;
an analyzer that analyzes the gas having passed through the filter element; and
a cleaning gas supply path which supplies cleaning gas for cleaning the filter element to an inside of the filter element from one end opening of the filter element,
wherein the filter element is configured such that the gas produced from the sample heated in the sample containing part passes through a side wall part of the filter element to the inside of the filter element, and
wherein the lower holding member holds a supply path forming member which is arranged inside an inner internal space of the sample containing part.

* * * * *